United States Patent
Hyde et al.

(10) Patent No.: US 10,076,241 B2
(45) Date of Patent: *Sep. 18, 2018

(54) VISION SYSTEM RESPONSIVE TO A PRESENCE OF A WEARABLE OPHTHALMIC ELEMENT

(71) Applicant: Elwha LLC, Bellevue, WA (US)

(72) Inventors: Roderick A. Hyde, Redmond, WA (US); Elizabeth A. Sweeney, Seattle, WA (US); Lowell L. Wood, Jr., Bellevue, WA (US)

(73) Assignee: Elwha LLC

( * ) Notice: Subject to any disclaimer, the term of this patent is extended or adjusted under 35 U.S.C. 154(b) by 121 days.

This patent is subject to a terminal disclaimer.

(21) Appl. No.: 14/982,689

(22) Filed: Dec. 29, 2015

(65) Prior Publication Data

US 2017/0181849 A1 Jun. 29, 2017

(51) Int. Cl.
| | |
|---|---|
| *G02C 7/00* | (2006.01) |
| *G02C 7/02* | (2006.01) |
| *G02C 7/04* | (2006.01) |
| *A61B 3/04* | (2006.01) |
| *A61B 3/10* | (2006.01) |
| *A61F 2/16* | (2006.01) |
| *G02C 7/08* | (2006.01) |

(52) U.S. Cl.
CPC ............ *A61B 3/04* (2013.01); *A61B 3/10* (2013.01); *A61F 2/1627* (2013.01); *G02C 7/04* (2013.01); *G02C 7/041* (2013.01); *G02C 7/08* (2013.01); *G02C 7/083* (2013.01)

(58) Field of Classification Search
CPC . G02C 7/04; G02C 7/041; G02C 7/08; G02C 7/083; G06F 3/013; G06F 3/0346; G06F 3/0317; G06F 3/016; A61B 3/10; A61F 2/14; A61F 9/08; A61F 2/1651; A61N 1/36046
USPC ......... 351/158, 159.03, 159.73, 159.34, 212, 351/206, 247; 345/8; 600/345; 623/6.31
See application file for complete search history.

(56) References Cited

U.S. PATENT DOCUMENTS

| | | |
|---|---|---|
| 6,197,057 B1 | 3/2001 | Peyman et al. |
| 8,197,539 B2 | 6/2012 | Nasiatka et al. |

(Continued)

OTHER PUBLICATIONS

Comstock, Jonah; "Novartis CEO comments, new patent shed light on Google's contact lens projects"; MobiHealthNews; Sep. 8, 2015; 5 Total Pages; Chester Street Publishing, Inc.; located at: http:mobihealthnews.com/46600/novartis-ceo-comments-new-patent-shed-light-on-googles-contact-lens-projects.

(Continued)

*Primary Examiner* — Mustak Choudhury

(57) ABSTRACT

Described embodiments include a vision system and a method. A vision system includes a receiver circuit configured to receive data indicative of a presence of a wearable ophthalmic element in an optical path incident on a vision correction device. The vision correction device includes an electronically controllable vision parameter and configured to be placed in an eye of a human subject. The vision system includes a controller circuit coupled to the vision correction device and configured to change the electronically controllable vision parameter of the vision correction device at least partially in response to the received data indicative of the presence of the wearable ophthalmic element in the optical path.

42 Claims, 8 Drawing Sheets

(56) References Cited

U.S. PATENT DOCUMENTS

| | | |
|---|---|---|
| 9,184,698 B1 | 11/2015 | Wiser et al. |
| 2005/0062679 A1* | 3/2005 | Aharoni .................. A61F 9/08 345/8 |
| 2005/0154457 A1 | 7/2005 | Aharoni et al. |
| 2005/0209691 A1 | 9/2005 | Aharoni et al. |
| 2005/0222680 A1 | 10/2005 | Aharoni et al. |
| 2015/0061990 A1* | 3/2015 | Toner .................... G06F 3/013 345/156 |
| 2015/0142107 A1 | 5/2015 | Pugh et al. |
| 2015/0250584 A1 | 9/2015 | Blum et al. |
| 2015/0320548 A1 | 11/2015 | Brady et al. |

OTHER PUBLICATIONS

Dhaliwal et al.; "Overview of Refractive Error"; Merck Manual; Bearing a date of Jan. 2015; 6 Total Pages; Merck Sharp & Dohme Corp., a subsidiary of Merck & Co.; located at: http://www.merckmanuals.com/professional/eye-disorders/refractive-error/overview-of-refractve-error.

"Lenses: Multi-Layer Diffractive Optical Element"; Canon Professional Network; Created on Nov. 9, 2015; 2 Total Pages; located at: http://cpn.canon-europe.com/content/education/infobank/lenses/multi_layer_diffractive_optical_element.do.

\* cited by examiner

FIG. 6

600 Vision System

610 Circuitry for receiving data indicative of a presence of a wearable ophthalmic element in an optical path incident on a vision correction device placed in an eye of a human subject.

620 Circuitry coupled to the vision correction device and for changing an electronically controllable vision parameter of the vision correction device at least partially in response to the received data indicative of the presence of the wearable ophthalmic element in the optical path.

630 Circuitry for broadcasting the data indicative of the presence of the wearable ophthalmic element in the optical path, the circuitry for broadcasting carried by a wearable structure configured to position or support the wearable ophthalmic element in the optical path.

640 Circuitry for receiving a human-input indicative of the presence of the wearable ophthalmic element in the optical path; and circuitry for broadcasting data indicative of the presence of the wearable ophthalmic element in the optical path.

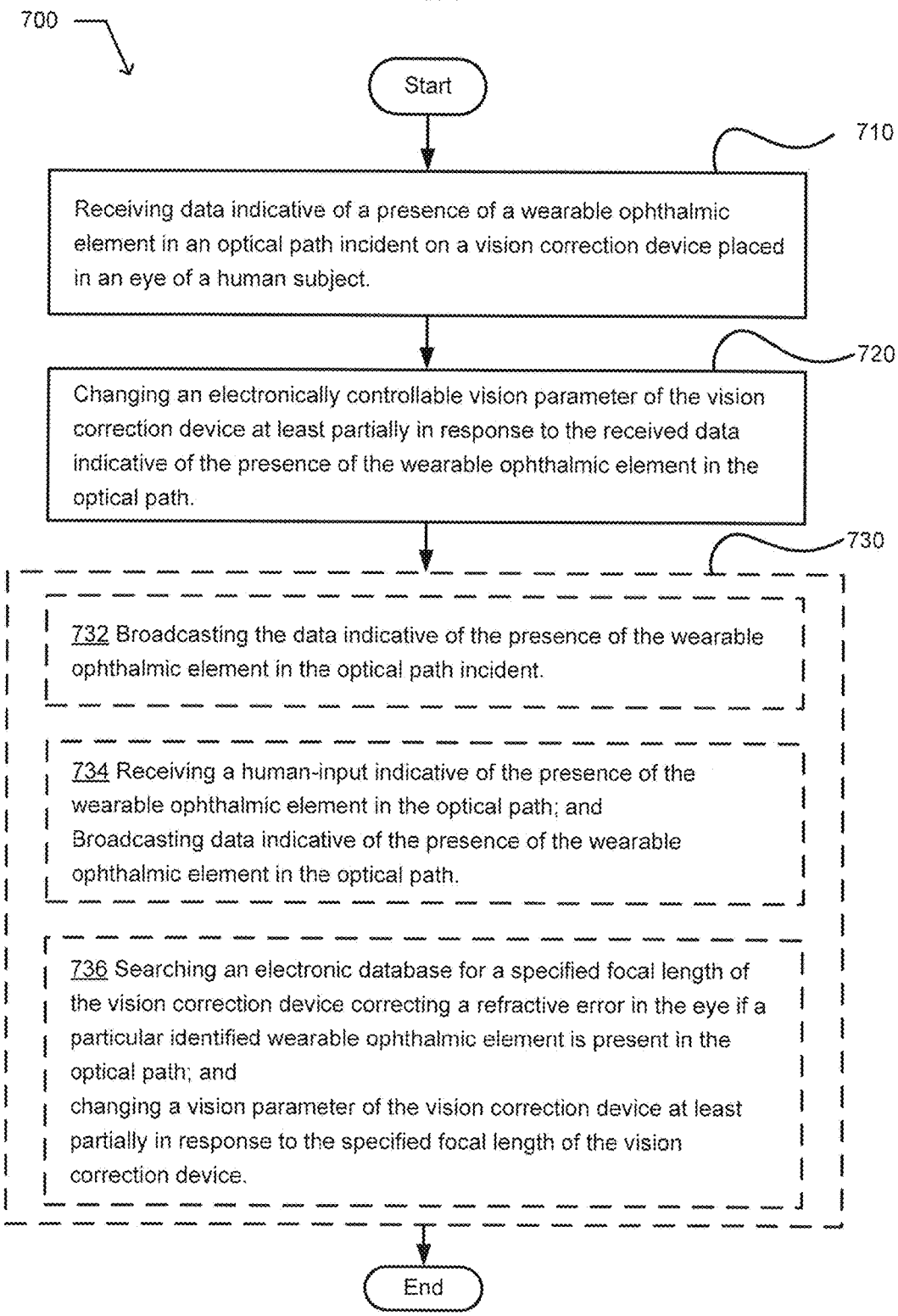

VISION SYSTEM RESPONSIVE TO A PRESENCE OF A WEARABLE OPHTHALMIC ELEMENT

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

Priority Applications

None.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

For example, and without limitation, an embodiment of the subject matter described herein includes a vision system. The vision system includes a receiver circuit configured to receive data indicative of a presence of a wearable ophthalmic element in an optical path incident on a vision correction device. The vision correction device includes an electronically controllable vision parameter and configured to be placed in an eye of a human subject. The vision system includes a controller circuit coupled to the vision correction device and configured to change the electronically controllable vision parameter of the vision correction device at least partially in response to the received data indicative of the presence of the wearable ophthalmic element in the optical path.

In an embodiment, the vision system includes a transmitter circuit configured to broadcast data indicative of the presence of the wearable ophthalmic element in the optical path. In an embodiment, the vision system includes a wearable structure configured to position or support the wearable ophthalmic element in the optical path incident on the vision correction device; and a transmitter circuit carried by the wearable structure and configured to broadcast data indicative of the presence of the wearable ophthalmic element in the optical path. In an embodiment, the vision system includes a wearable structure configured to position or support the wearable ophthalmic element in the optical path incident on the vision correction device; and a human-interface circuit coupled to the wearable structure and configured to (i) receive a human-input indicative of a presence of the wearable ophthalmic element in the optical path, and (ii) broadcast data indicative of the presence of the wearable ophthalmic element in the optical path. In an embodiment, the vision system includes a sensor circuit configured to detect and transmit data indicative of the presence of the wearable ophthalmic element in the optical path. In an embodiment, the vision system includes a correction manager circuit configured to search an electronic database for a specified focal length of the wearable ophthalmic element. In an embodiment, the vision system includes a database stored on a non-transitory computer readable storage media and specifying a respective focal length of the wearable ophthalmic element for at least two identified wearable ophthalmic elements.

For example, and without limitation, an embodiment of the subject matter described herein includes a vision system. The vision system includes circuitry for receiving data indicative of a presence of a wearable ophthalmic element in an optical path incident on a vision correction device placed in an eye of a human subject. The vision system includes circuitry coupled to the vision correction device and for changing an electronically controllable vision parameter of the vision correction device at least partially in response to the received data indicative of the presence of the wearable ophthalmic element in the optical path.

In an embodiment, the vision system includes circuitry for broadcasting the data indicative of the presence of the wearable ophthalmic element in the optical path, the circuitry for broadcasting carried by a wearable structure configured to position or support the wearable ophthalmic element in the optical path. In an embodiment, the vision system includes circuitry for receiving a human-input indicative of a presence of the wearable ophthalmic element in the optical path; and circuitry for broadcasting data indicative of the presence of the wearable ophthalmic element in the optical path from a transmitter circuit carried by a wearable structure configured to position or support the ophthalmic element in the optical path.

For example, and without limitation, an embodiment of the subject matter described herein includes a method. The method includes receiving data indicative of a presence of a wearable ophthalmic element in an optical path incident on a vision correction device placed in an eye of a human subject. The method includes changing an electronically controllable vision parameter of the vision correction device at least partially in response to the received data indicative of the presence of the wearable ophthalmic element in the optical path.

In an embodiment, the method includes broadcasting the data indicative of the presence of the wearable ophthalmic element in the optical path incident. In an embodiment, the method includes broadcasting the data indicative of the presence of the wearable ophthalmic element in the optical path incident from a transmitter circuit carried by a wearable structure configured to position or support the wearable ophthalmic element in the optical path. In an embodiment, the method includes receiving a human-input indicative of the presence of the wearable ophthalmic element in the optical path; and broadcasting data indicative of the presence of the wearable ophthalmic element in the optical path from a transmitter circuit carried by a wearable structure configured to position or support the ophthalmic element in the optical path.

In an embodiment, the method includes searching an electronic database for a specified focal length of the vision correction device correcting a refractive error in the eye if a particular identified wearable ophthalmic element is present in the optical path; and changing a vision parameter of the vision correction device at least partially in response to the specified focal length of the vision correction device.

For example, and without limitation, an embodiment of the subject matter described herein includes a system. The system includes an ophthalmic lens configured to aid vision in an eye of a human. The system includes a wearable structure configured to position or support the ophthalmic lens in an optical path incident on a vision correction device placed in the eye of the human. The system includes a transmitter circuit coupled to the wearable structure and configured to broadcast data indicative of a presence of the ophthalmic lens. In an embodiment, the system includes a sensor circuit configured to detect if the wearable structure is being worn by the human.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 6 illustrates an example vision system 600 in which embodiments may be implemented;

FIG. 7 illustrates an example operational flow 700 in which embodiments may be implemented.

DETAILED DESCRIPTION

Figure 1:
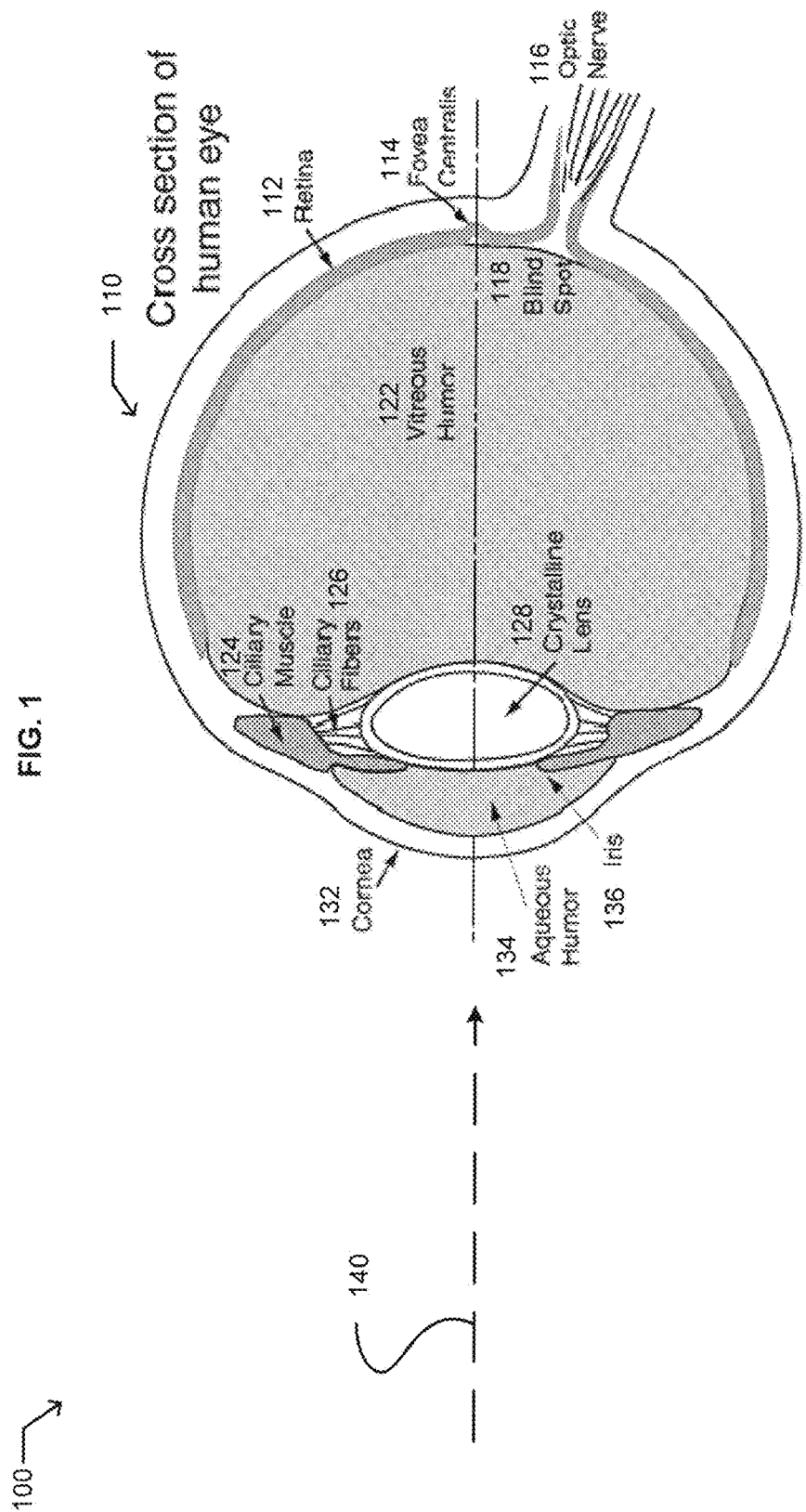
FIG. 1 schematically illustrates an example environment 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

This application makes reference to technologies described more fully in U.S. patent application Ser. No. 14/807,673, entitled INTRAOCULAR LENS SYSTEMS AND RELATED METHODS, naming Roderick A. Hyde et al. as inventors, filed on 23 Jul. 2015, is related to the present application. That application is incorporated by reference herein, including any subject matter included by reference in that application.

This application makes reference to technologies described more fully in U.S. patent application Ser. No. 14/807,719, entitled INTRAOCULAR LENS DEVICES, SYSTEMS AND RELATED METHODS, naming Roderick A. Hyde et al. as inventors, filed on 23 Jul. 2015, is related to the present application. That application is incorporated by reference herein, including any subject matter included by reference in that application.

This application makes reference to technologies described more fully in U.S. patent application Ser. No. 14/807,756, entitled INTRAOCULAR LENS SYSTEMS AND RELATED METHODS, naming Jesse R. Cheatham, III. et al. as inventors, filed on 23 Jul. 2015, is related to the present application. That application is incorporated by reference herein, including any subject matter included by reference in that application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various implementations by which processes and/or systems and/or other technologies described herein can be effected (e.g., hardware, software, and/or firmware), and that the preferred implementation will vary with the context in which the processes and/or systems and/or other technologies are deployed. For example, if an implementer determines that speed and accuracy are paramount, the implementer may opt for a mainly hardware and/or firmware implementation; alternatively, if flexibility is paramount, the implementer may opt for a mainly software implementation; or, yet again alternatively, the implementer may opt for some combination of hardware, software, and/or firmware. Hence, there are several possible implementations by which the processes and/or devices and/or other technologies described herein may be effected, none of which is inherently superior to the other in that any implementation to be utilized is a choice dependent upon the context in which the implementation will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to implement an operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described below. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, module, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will also recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will further recognize that at least a portion of the devices and/or processes described herein can be integrated into an image processing system. A typical image processing system may generally include one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch-sensitive screen or display surface, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will likewise recognize that at least some of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch-sensitive screen or display surface, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

FIG. 1 schematically illustrates an example environment 100 in which embodiments may be implemented. The environment includes a cross section of a human eye 110 and an optical path 140 incident on crystalline lens 128 of the eye. The human eye includes retina 112, fovea centralis 114, optic nerve 116, and blind spot 118. The human eye includes a vitreous humor 122, ciliary muscle 124, ciliary fibers 126, and crystalline lens 128. The human eye includes cornea 132, aqueous humor 134, and iris 136.

Figure 2:
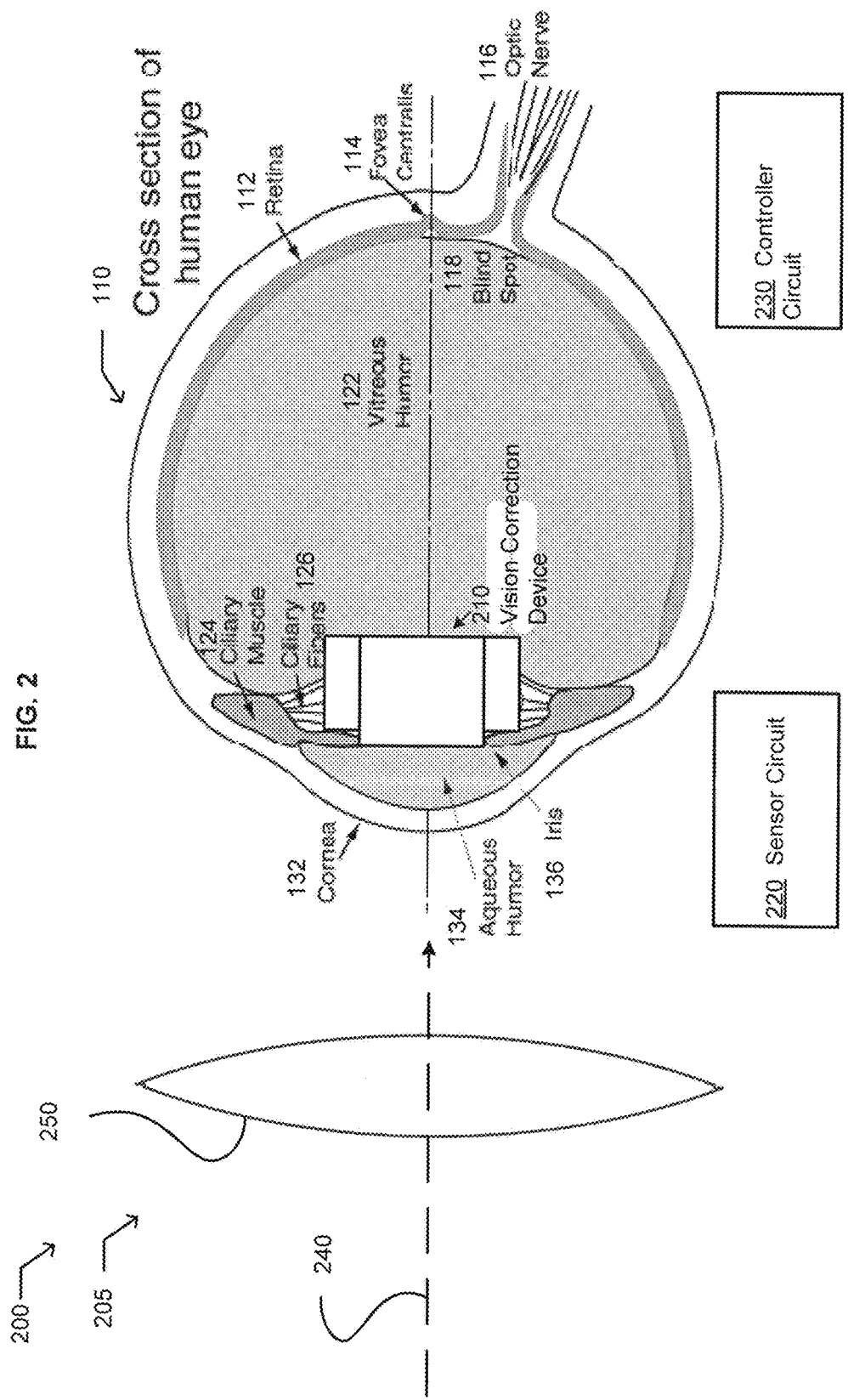
FIG. 2 schematically illustrates an example environment 200 in which embodiments may be implemented.

FIG. 2 schematically illustrates an example environment 200 in which embodiments may be implemented. The example environment includes a vision system 205 and the human eye 110. The vision system includes a sensor circuit 220 configured to detect a presence of a wearable ophthalmic element 250 in an optical path 240 incident on a vision correction device 210. The vision correction device includes an electronically controllable vision parameter and is configured to be placed in the eye 110 of a human subject. In an embodiment, the wearable ophthalmic element 250 may include eye glasses or contacts. The vision system includes a controller circuit 230 coupled to the vision correction device and configured to change the electronically controllable vision parameter of the vision correction device at least partially in response to the detected presence of the wearable ophthalmic element in the optical path. For example, in an embodiment, the vision system includes the vision correction device having adjustable properties or parameters. In an example, the vision system determines if the human subject is wearing an ophthalmic element, such as eyeglasses or contact lenses, and makes adjustments to the vision correction device based on this determination.

In an embodiment, the sensor circuit 220 includes a sensor circuit configured to detect the presence of the wearable ophthalmic element 250 at least partially based on a convergence change in light rays in the optical path 240. For example, a convergence change may include a negative convergence or divergence change. In an embodiment, the sensor circuit is further configured to measure the convergence change in the light rays in the optical path. For example, the measurement of the convergence change will describe the focal power or transmission of the eyeglass or contact lens. For example, the vision system may detect a presence of eyeglasses or contact lens by emitting a light and detecting a return beam from a retroreflector on the eyeglasses or contact lens. In an embodiment, the sensor circuit is configured to detect the presence of a wearable ophthalmic element at least partially based on a rapid or sudden convergence change in the light rays in the optical path. For example, a rapid or sudden change in the convergence of the incident light may be indicative of the human subject putting on eyeglasses or contact lens. For example, a sudden change in an intensity or spectral content of the incident light may be indicative of the human subject putting on eyeglasses or contact lens. In an embodiment, for example, the controller circuit 230 is told by the sensor circuit that the human is wearing eyeglasses or contact lenses and the controller then takes an appropriate action to maintain a focus in the eye 110. In an embodiment, the sensor circuit is configured to detect the presence of a wearable ophthalmic element and quantitatively measure a convergence change in light rays in the optical path resulting from the presence of the wearable optical element in the optical path. In an embodiment, the sensor circuit is configured to detect the presence of a wearable ophthalmic element and quantitatively measure a convergence change upstream of the vision correction device in light rays in the optical path resulting from the presence of the wearable optical element in the optical path. In this embodiment, the controller circuit is configured to change the electronically controllable vision parameter at least partially in response to the detected presence of a wearable ophthalmic element and the quantitatively measured convergence change. In an embodiment, the sensor circuit includes a sensor circuit configured to detect the presence of the wearable ophthalmic element at least partially in response to a change in a characteristic of light rays in the optical path. For example, a characteristic of the light rays may include a spectrum change or a broadband change in amount of light. In an embodiment, the sensor circuit includes a sensor circuit configured to detect the presence of the wearable ophthalmic element at least partially in response to a change in a transmission of light rays in the optical path. In an embodiment, the sensor circuit includes a photodetector configured to detect the presence of the wearable ophthalmic element in the optical path incident on the vision correction device. In an embodiment, the photodetector includes a broadband or a spectrally limited photodetector. In an embodiment, the sensor circuit includes a proximity sensor configured to detect the presence of the wearable ophthalmic element in the optical path. In an embodiment, the proximity sensor includes a capacitive or optical proximity sensor. In an embodiment, the sensor circuit includes an imaging system configured to detect the presence of the wearable ophthalmic element in the optical path. For example, in an embodiment, the imaging device in the vision correction device "sees" the wearable device. For example, the imaging circuit may include a photodetector, or a photodetector and lens. For example, the imaging circuit may include a light source generating a beam reflecting off the wearable ophthalmic element that is detected. For example, the reflected beam may be detected by a photodetector, or a photodetector and lens. For example, the sensor circuit may include an ultrasound source generating a beam reflecting off the wearable ophthalmic element and a sensor configured to detect the reflected ultrasonic beam. In an embodiment, the sensor circuit includes a radiation source and a radiation detector configured to detect the presence of the wearable ophthalmic element in the optical path. For example, the radiation source may include an optical or an ultrasound radiation source. For example, in an embodiment, the radiation source generates radiation that bounces off the wearable ophthalmic element and is detected.

In an embodiment, the sensor circuit 220 includes a non-volatile computer storage media. In an embodiment, the sensor circuit is configured to store a characteristic of light rays previously in the optical path 240 and detect the presence of the wearable ophthalmic element 250 responsive to a temporal change in the characteristic of light rays in the optical path.

In an embodiment, the vision correction device 210 includes the sensor circuit 220. In an embodiment, the vision correction device includes a vision correction device having an electronically variable focal length parameter. In an embodiment, the vision correction device includes an electronically controllable focal length parameter. For example, the electronically controllable focal length parameter may include electronically controllable index of refraction. In an embodiment, the vision correction device includes an intraocular lens device implanted in the eye 110 of the human subject. In an embodiment, the vision correction device includes an intraocular lens device implanted in the aphakic eye 110 of the human subject to replace the absent lens, e.g., after surgical removal of a cataract. In an embodiment, the intraocular lens device includes a phakic intraocular lens implanted over the natural lens of the eye 110 of the human subject. In an embodiment, the intraocular lens device may include two or more individual intraocular lens. In an embodiment, an intraocular lens device may include a single vision, a monofocal, or a toric lens device. In an embodiment, a vision correction device may have more than one feature. In an embodiment, a vision correction device may include a first vision correction device having a first electronically controllable vision parameter placed in the eye 110 and a second vision correction device having a second electronically controllable vision parameter placed in another eye of the human subject. For example, the controller circuit 230 may coordinate a change of the respective electronically controllable vision parameters to compensate for presbyopia present with refractive errors. In an embodiment, the vision correction device includes an accommodating intraocular lens. For example, in an embodiment, accommodation is a process that enables the eye to adjust its focusing power to provide clear vision at all distances. In a normal eye, this dynamic process of accommodation adjusts the focusing power of the eye by changing the thickness of the eye's natural lens. When the ciliary muscle is relaxed, the lens flattens to enable clear distance vision. When the ciliary muscle contracts, the lens thickens, becoming more curved for added magnification for clear near vision. In an embodiment, an accommodating intraocular lens interacts with the structure of the eye to provide both clear distance vision and clear near vision. In an embodiment, the intraocular lens device includes a multifocal intraocular lens device. In an embodiment, the intraocular lens device includes an autofocusing intraocular lens device. In an embodiment, the intraocular lens device includes a dynamically variable focal length intraocular lens device.

In an embodiment, the vision correction device 210 is configured to be worn on the eye 110 of the human subject. In an embodiment, the vision correction device includes a multifocal vision correction device. In an embodiment, the vision correction device includes an autofocus vision correction device. In an embodiment, the vision correction device is configured to at least partially correct a refractive error in the eye. In an embodiment, the vision correction device is configured to at least partially compensate for a refractive error in the eye. For example, a refractive error may include astigmatism, near sightedness, or far sightedness. In an embodiment, refractive errors are vision problems that happen when the shape of the eye keeps the eye from focusing well. The cause could be the length of the eyeball (longer or shorter), changes in the shape of the cornea, or aging of the lens. Four common refractive errors are Myopia, or nearsightedness—clear vision close up but blurry in the distance; Hyperopia, or farsightedness—clear vision in the distance but blurry close up; Presbyopia—inability to focus close up as a result of aging; and Astigmatism—focus problems caused by the cornea.

In an embodiment, the wearable ophthalmic element 250 includes an ophthalmic lens. In an embodiment, the ophthalmic lens includes a corrective lens or a non-corrective lens worn in front of the eye 110. In an embodiment, the corrective lens includes spectacles and contact lenses. In an embodiment, the non-corrective lens includes "non-corrective lenses" such as sunglasses, safety glasses, and cosmetic lenses. In an embodiment, the ophthalmic lens includes a supra-ocular corrective lens or non-corrective lens. In an embodiment, the wearable ophthalmic element includes a contact lens configured to fit over the cornea 132 of the eye. In an embodiment, the wearable ophthalmic element includes a contact lens configured to fit over the cornea of the eye and float on a tear of the eye. In an embodiment, the wearable ophthalmic element is configured to provide a magnification. For example, the magnification may include magnification provided by a loupe designed to provide high resolution at a close distance.

In an embodiment, the vision parameter of the vision correction device 210 includes a focal length parameter. In an embodiment, the vision parameter of the vision correction device includes an optical transmissivity parameter.

In an embodiment, the controller circuit 230 is configured to at least partially correct a refractive error in the eye 110 by changing the electronically controllable vision parameter at least partially in response to the detected presence of the wearable ophthalmic element 250. For example, in an embodiment, the controller circuit reduces the focal power of the vision correction device to take into account extra convergence due to the ophthalmic element. For example, in an embodiment, the controller circuit varies its transmissivity (total or spectral) to take into account a transmissivity change due to the ophthalmic element, such as an eyeglass or contact lens. For example, in an embodiment, the controller circuit reduces the focal power of the vision correction device. In an embodiment, the controller circuit includes a controller circuit configured at least partially in response to the detected presence of the wearable ophthalmic element to (i) at least partially correct a refractive error in the eye by changing the electronically controllable vision parameter of the vision correction device and (ii) at least partially correct another refractive error in another eye of the human subject by changing another electronically controllable vision parameter of another vision correction device placed in another eye of the human subject. In an embodiment, the controller circuit is configured not to change a vision parameter of the vision correction device in response to an override signal. For example, the controller circuit can be told to ignore the presence of an eyeglass or contact lens (i.e., even though it is setup to detect this, it is instructed to ignore the presence). For example, the controller circuit can be told to ignore the presence of an eyeglass or contact lens because the human subject may put on eyeglasses or contacts so that they can get extra optical power. In an embodiment, the override signal includes an override signal generated by the wearable ophthalmic element. In an embodiment, the override signal includes an override signal initiated by the human subject. In an embodiment, the controller circuit is operatively coupled with the vision correction device. For example, the controller circuit may be electrically or wirelessly operatively coupled with the vision correction device. In an embodiment, the controller circuit is configured to be carried by the human. In an embodiment, the vision correction device 210 includes the controller circuit.

In an embodiment, the system 205 includes the wearable ophthalmic element 250. In an embodiment, the system includes the wearable ophthalmic element 250 and the vision correction device. In an embodiment, the system 205 includes the vision correction device 210.

Figure 3:
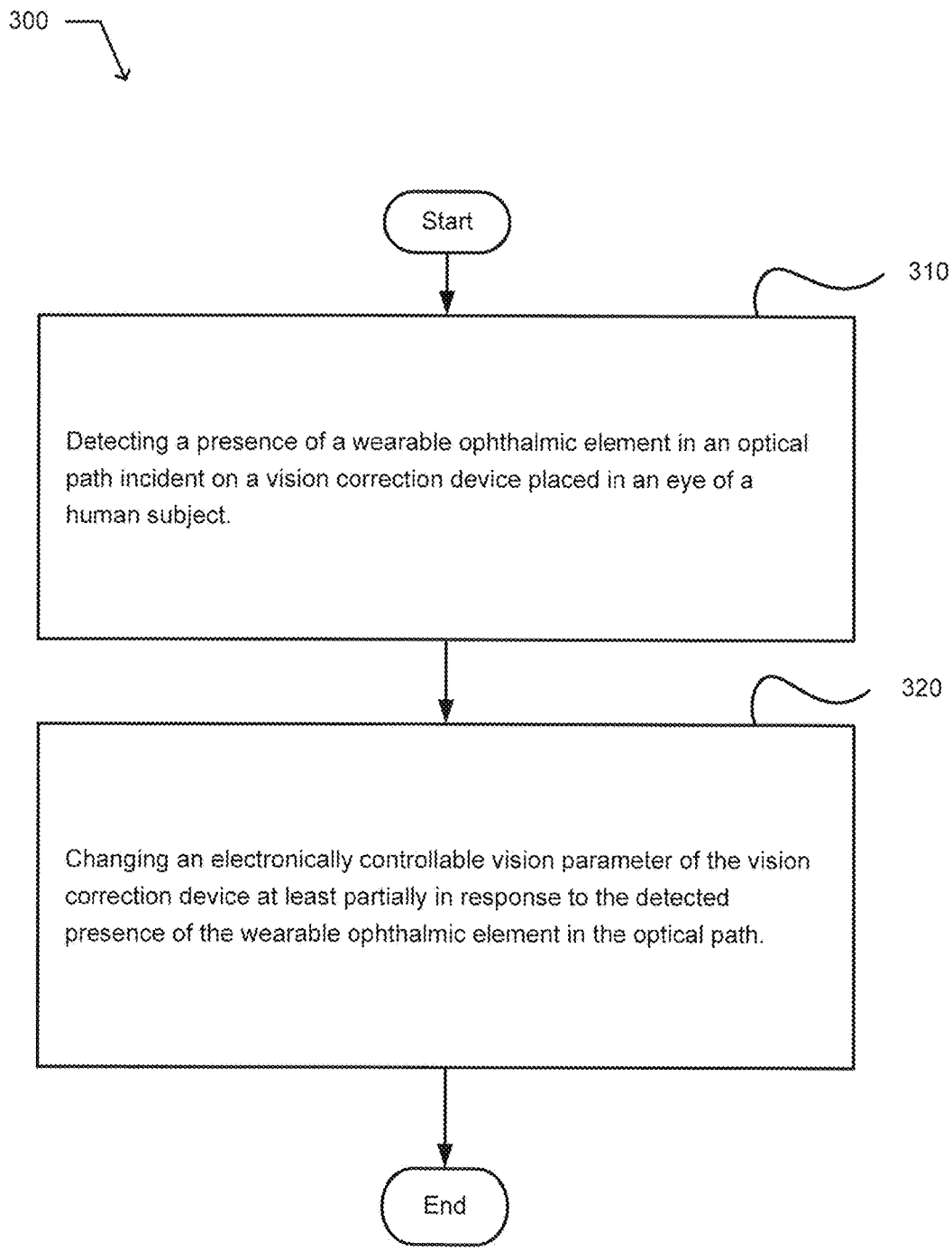
FIG. 3 illustrates an example operational flow 300.

FIG. 3 illustrates an example operational flow 300. After a start operation, the operational flow includes a discovery operation 310. The discovery operation includes detecting a presence of a wearable ophthalmic element in an optical path incident on a vision correction device placed in an eye of a human subject. In an embodiment, the discovery operation may be implemented using the sensor circuit 220 described in conjunction with FIG. 2. A vision parameter adjustment operation 320 includes changing an electronically controllable vision parameter of the vision correction device at least partially in response to the detected presence of the wearable ophthalmic element in the optical path. In an embodiment, the vision parameter adjustment operation may be implemented using the vision correction device 210 described in conjunction with FIG. 2. The operational flow includes an end operation.

Figure 4:
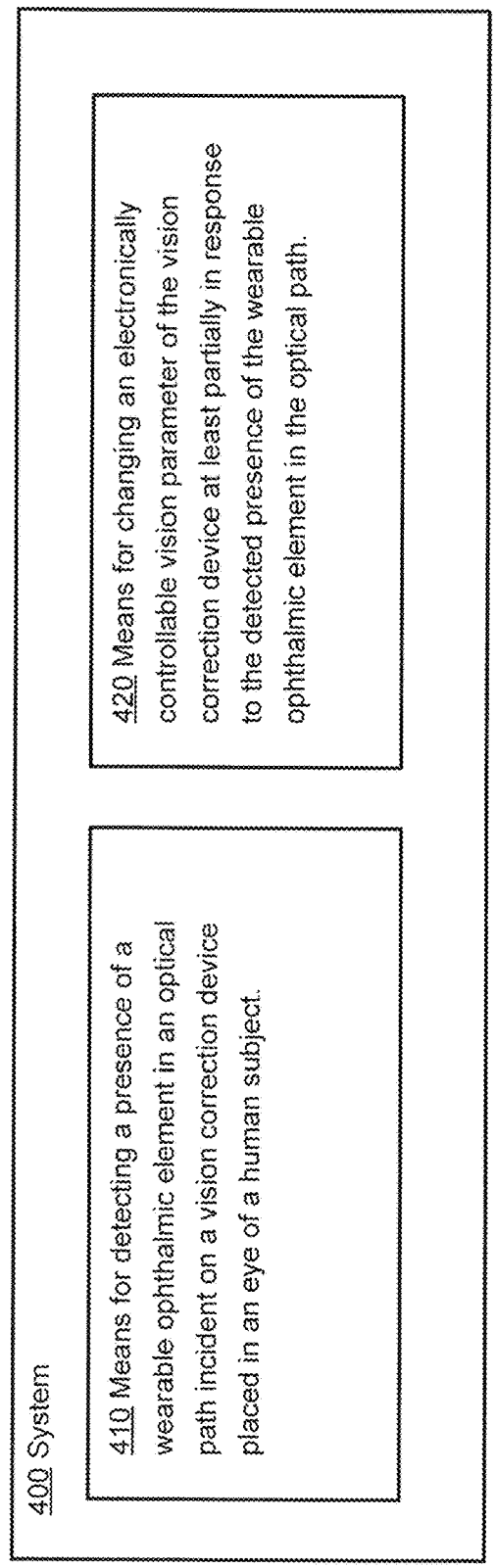
FIG. 4 includes an example vision system 400.

FIG. 4 includes an example vision system 400. The vision system includes means for detecting 410 a presence of a wearable ophthalmic element in an optical path incident on a vision correction device placed in an eye of a human subject. The system includes means for changing 420 an electronically controllable vision parameter of the vision correction device at least partially in response to the detected presence of the wearable ophthalmic element in the optical path.

Figure 5:
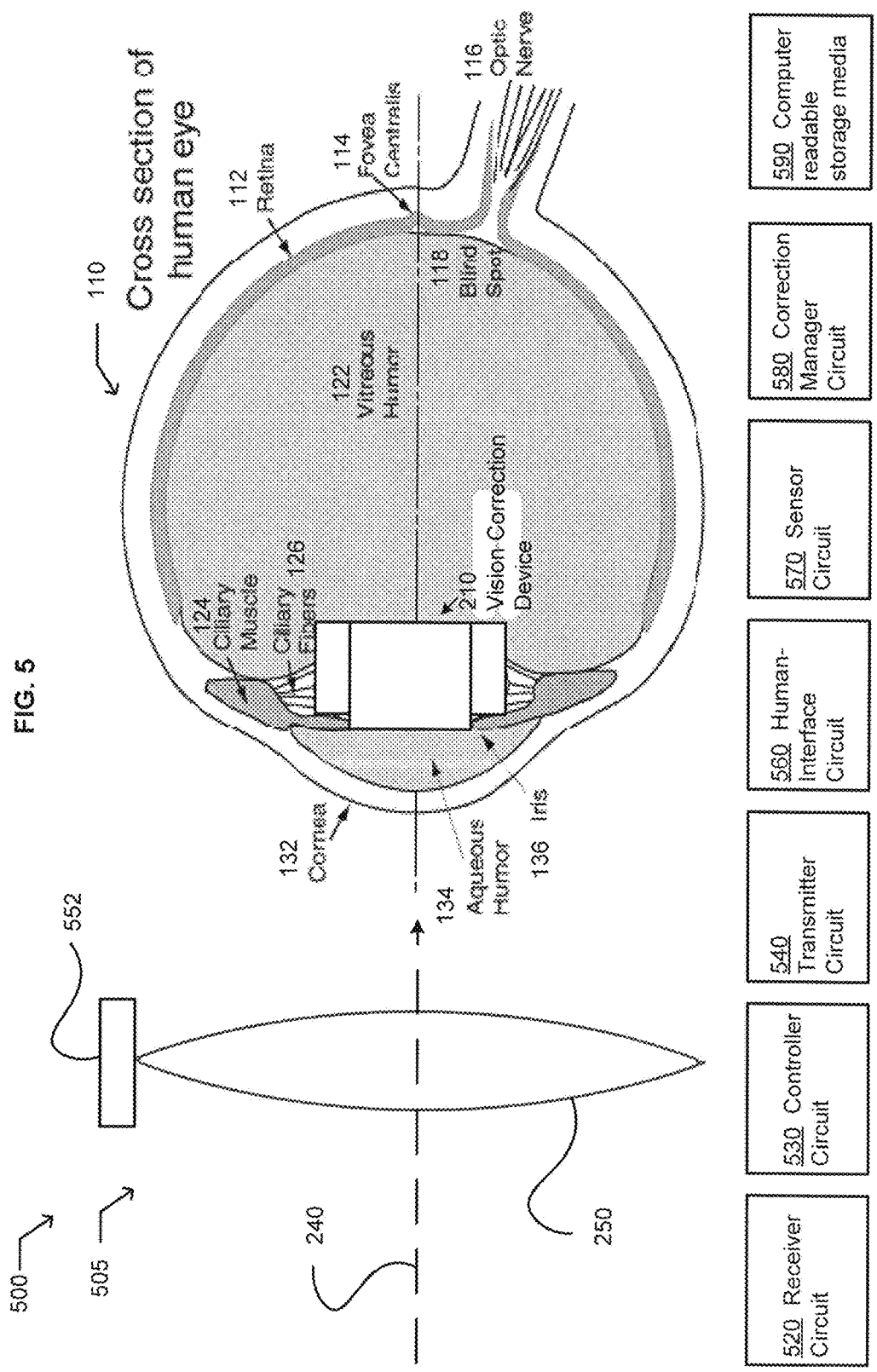
FIG. 5 illustrates an example environment 500 in which embodiments may be implemented.

FIG. 5 illustrates an example environment 500 in which embodiments may be implemented. The example environment includes a vision system 505 and the human eye 110. The vision system includes a receiver circuit 520 configured to receive data indicative of a presence of the wearable ophthalmic element 250 in the optical path 240 incident on the vision correction device 210 placed in the eye of a human subject. The vision correction device includes an electronically controllable vision parameter and is configured to be placed in an eye of a human subject. In an embodiment, the electronically controllable vision parameter includes an electronically controllable focal length. In an embodiment, the electronically controllable focal length includes an electronically controllable spherical focal length. In an embodiment, the electronically controllable focal length includes an electronically controllable cylindrical focal length. In an embodiment, the data includes data indicative of a presence of the wearable ophthalmic element in or a removal of the wearable ophthalmic element from the optical path. In an embodiment, the receiver circuit is carried by the vision correction device. In an embodiment, the receiver circuit is configured to receive data from an external imaging device, such as a camera or imaging device, or from a device associated with the wearable ophthalmic element.

The vision system 505 includes a controller circuit 530 coupled to the vision correction device 210 and configured to change the electronically controllable vision parameter of the vision correction device at least partially in response to the received data indicative of the presence of the wearable ophthalmic element 250 in the optical path 240. In an embodiment, the controller circuit is coupled to the vision correction device and configured to change the electronically controllable focal length of the vision correction device at least partially in response to the received data indicative of the presence of the wearable ophthalmic element in or the removal of the wearable ophthalmic element from the optical path. In an embodiment, the received data tells the controller circuit that the patient is wearing eyeglasses or contact lenses. In an embodiment, the data may be originated by the human, or by eyeglass or contact lens worn by the human. In an embodiment, the data may be communicated to the receiver circuit by a radiofrequency link, an optical link, a wired link, or some other link or device. In an embodiment, eyeglasses or contact lenses worn by the human may tell the vision correction device that they are being worn by the human. For example, an eyeglass frame or one of the contacts may include RFID. For example, an eyeglass frame or one of the contacts may emit a signal, light, etc. In an embodiment, the controller circuit may reduce the focal power of the vision correction device given a presence of eyeglasses or contacts in the optical path.

In an embodiment, the data includes human-inputted data indicative of the presence of the ophthalmic element 250 in the optical path 240. In an embodiment, the data includes human-inputted data indicative of the presence of the ophthalmic element in or the removal of the ophthalmic element from the optical path. In an embodiment, the data includes a data signal indicative of the presence of an ophthalmic element in the optical path. In an embodiment, the data includes a data signal indicative of the presence of an ophthalmic element in or the removal of the ophthalmic element from the optical path. In an embodiment, the data signal is originated or transmitted by an electronic device physically associated with or coupled to the wearable ophthalmic element or a wearable frame. For example, the data signal may be originated by a device external to the vision correction device. In an embodiment, the data signal includes a radiofrequency band data signal, an ultrasound frequency band data signal, or an optical frequency band data signal. In an embodiment, the data signal is transmitted by an RFID electronic device coupled or physically associated with the wearable ophthalmic element in response to a query response received from associated with the ophthalmic element. In an embodiment, the data signal is transmitted by a sensor circuit 570 configured to detect the presence of a wearable ophthalmic element in the optical path incident on the vision correction device. In an embodiment, the data includes data indicative of a focal length or optical transmissivity of the wearable ophthalmic element. In an embodiment, the data includes data indicative of an identification of the wearable ophthalmic element. In an embodiment, the data indicative of an identification of the wearable ophthalmic element includes an identification of a brand name, a manufacturer, a spherical parameter, or cylindrical parameter of the wearable ophthalmic element.

In an embodiment, the controller circuit 530 is configured to correct a refractive error in the eye 110 by changing the electronically controllable vision parameter of the vision correction device 210 at least partially in response to the received data indicative of the presence of the wearable ophthalmic element 250 in the optical path 240. In an embodiment, the controller circuit is configured to not change the vision parameter of the vision correction device responsive to an override signal.

In an embodiment, the system 505 includes a transmitter circuit 540 configured to broadcast data indicative of the presence of the wearable ophthalmic element 250 in the optical path 240. For example, the transmitter circuit may be operatively coupled with the vision correction device 210, associated with the wearable ophthalmic element, or freestanding. In an embodiment, the system includes a wearable structure 552 configured to position or support the ophthalmic element in the optical path incident on the vision correction device. In this embodiment, the system includes the transmitter circuit carried by the wearable structure and configured to broadcast data indicative of a presence of the wearable ophthalmic element in the optical path. In an embodiment, the system includes the wearable structure 552 configured to position or support the ophthalmic element in the optical path incident on the vision correction device. In this embodiment, the system includes a human-interface circuit 560 coupled to the wearable structure and configured to (i) receive a human-input indicative of a presence of the ophthalmic element in the optical path, and (ii) broadcast data indicative of the presence of the wearable ophthalmic element in the optical path.

In an embodiment, the system 505 includes a sensor circuit 570 configured to detect and transmit data indicative of the presence of the wearable ophthalmic element in or a removal of the wearable ophthalmic element from the optical path. For example, the sensor circuit may include an external imaging device that sees if the human is wearing the wearable structure. For example, the sensor circuit may be carried by the vision correction device. In an embodiment, the system further includes a correction manager circuit 580 configured to search an electronic database for a link to a specified focal length or transmissivity of the wearable ophthalmic element. In an embodiment, the controller circuit 530 includes a controller circuit coupled to the vision correction device 210 and configured to change a vision parameter of the vision correction device at least partially in response to the specified focal length or transmissivity of the wearable ophthalmic element.

In an embodiment, the system 505 includes a database stored on a non-transitory computer storage media 590 and specifying a respective focal length of the wearable ophthalmic element for at least two identified wearable ophthalmic elements. For example, the non-transitory computer storage media may include volatile and nonvolatile memory such as ROM or RAM. For example, the non-transitory computer storage media may include removable or non-removable, or volatile or nonvolatile computer storage media products. In an embodiment, the wearable ophthalmic element 250 includes an eyeglass lens. In an embodiment, the wearable ophthalmic element includes a contact lens.

FIG. 6 illustrates an example vision system 600 in which embodiments may be implemented. The system includes circuitry 610 for receiving data indicative of a presence of a wearable ophthalmic element in or a removal of the wearable ophthalmic element from an optical path incident on a vision correction device placed in an eye of a human subject. The system includes circuitry 620 coupled to the vision correction device and configured for changing an electronically controllable vision parameter of the vision correction device at least partially in response to the received data indicative of the presence of the wearable ophthalmic element in or the removal of the wearable ophthalmic element from the optical path.

In an embodiment, the system 600 includes circuitry 630 for broadcasting the data indicative of the presence of the wearable ophthalmic element in the optical path. The circuity for broadcasting is carried by a wearable structure configured to position or support the wearable ophthalmic element in the optical path.

In an embodiment, the system 600 includes circuitry 640 for (i) receiving a human-input indicative of the presence of the wearable ophthalmic element 250 in the optical path 240; and (ii) broadcasting data indicative of the presence of the wearable ophthalmic element in the optical path from a transmitter circuit carried by a wearable structure configured to position or support the wearable ophthalmic element in the optical path.

FIG. 7 illustrates an example operational flow 700 in which embodiments may be implemented. After a start operation, the operational flow includes a reception operation 710. The reception operation includes receiving data indicative of a presence of a wearable ophthalmic element in an optical path incident on a vision correction device placed in an eye of a human subject. In an embodiment, the reception operation may be implemented using the receiver circuit 520 described in conjunction with FIG. 5. A vision parameter adjustment operation 720 includes changing an electronically controllable vision parameter of the vision correction device at least partially in response to the received data indicative of the presence of the wearable ophthalmic element in the optical path. In an embodiment, the vision parameter adjustment operation may be implemented by the control circuit 530 changing the electronically controllable vision parameter of the vision correction device 210 described in conjunction with FIG. 5. The operational flow includes an end operation.

In an embodiment, the operational flow 700 includes at least one additional operation 730. In an embodiment, the at least one additional operation includes an operation 732 broadcasting the data indicative of the presence of the wearable ophthalmic element in the optical path incident. In an embodiment, the at least one additional operation includes an operation broadcasting the data indicative of a presence of the wearable ophthalmic element in the optical path incident from a transmitter circuit carried by a wearable structure configured to position or support the wearable ophthalmic element in the optical path (not illustrated). In an embodiment, the at least one additional operation includes an operation 734 (i) receiving a human-input indicative of the presence of the wearable ophthalmic element in the optical path; and (ii) broadcasting data indicative of the presence of the wearable ophthalmic element in the optical path from a transmitter circuit carried by a wearable structure configured to position or support the ophthalmic element in the optical path. In an embodiment, the at least one additional operation includes an operation 736 (i) searching an electronic database for a specified focal length of the vision correction device correcting a refractive error in the eye if a particular identified wearable ophthalmic element is present in the optical path; and (ii) changing a vision parameter of the vision correction device at least partially in response to the specified focal length of the vision correction device.

Figure 8:
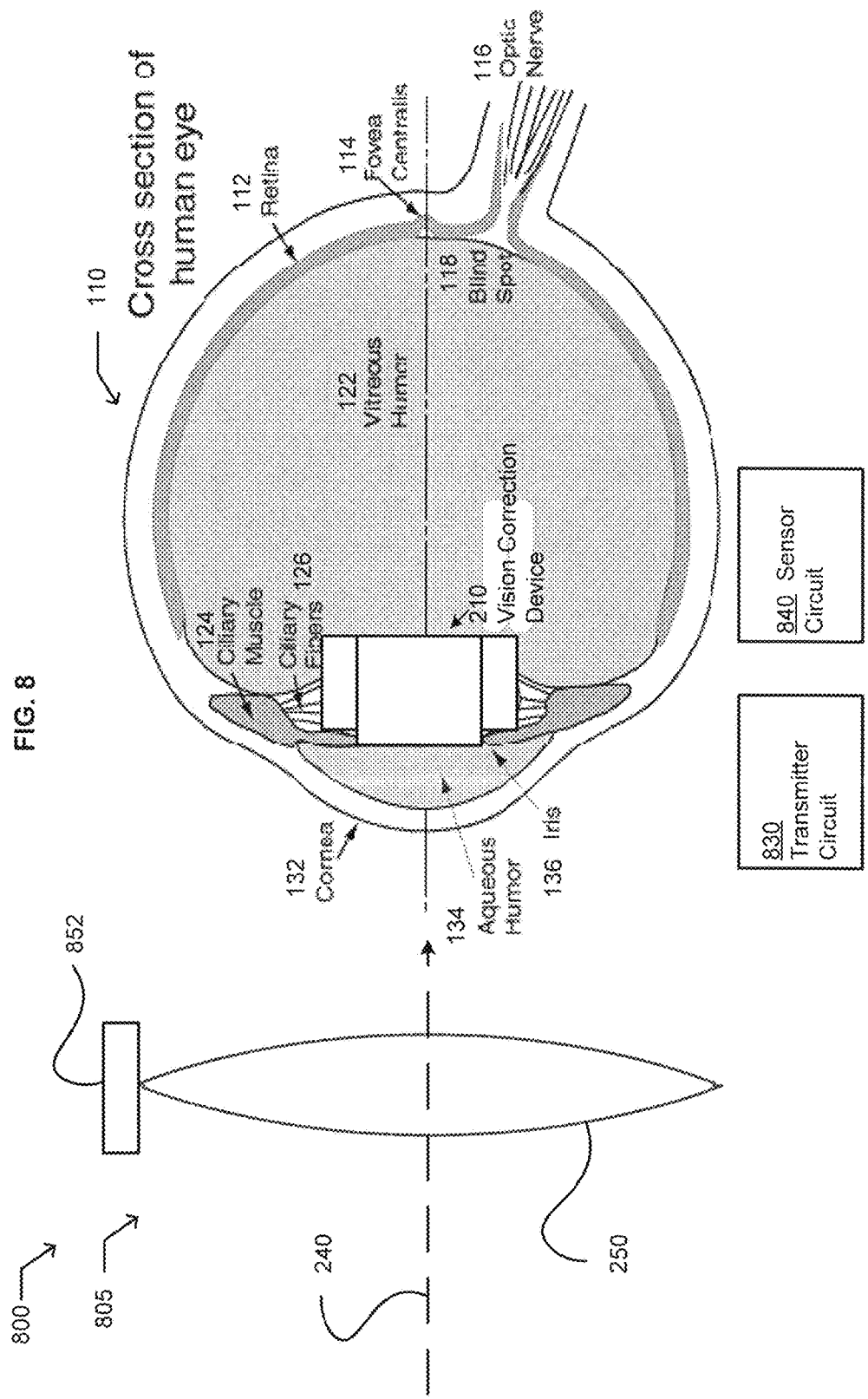
FIG. 8 illustrates an example environment 800 in which embodiments may be implemented.

FIG. 8 illustrates an example environment 800 in which embodiments may be implemented. The environment includes the eye 110 of a human and a system 805. The system includes the ophthalmic lens 250 configured to aid vision in the eye 110 of the human. The system includes a wearable structure 852 configured to position or support the ophthalmic lens in the optical path 240 incident on the vision correction device 210 placed in the eye of the human. The system includes a transmitter circuit 830 coupled to the wearable structure and configured to wirelessly broadcast data indicative of a presence of the ophthalmic lens. In an embodiment, the transmitter circuit may be carried by the wearable structure, or may be a freestanding transmitter circuit, such as configured for mounting on a wall.

In an embodiment, the system 805 includes a sensor circuit 840 configured to detect if the wearable structure 852 is being worn by the human. In an embodiment, the sensor circuit is further configured to initiate the broadcast of data indicative of the presence of the ophthalmic lens by the transmitter circuit.

In an embodiment, the ophthalmic lens 250 includes a single vision lens. In an embodiment, the ophthalmic lens includes a bifocal vision lens. In an embodiment, the wearable structure 852 includes a spectacle structure configured to position or support the ophthalmic lens on or from the head of the human. In an embodiment, the spectacle structure includes an ear piece configured to position or support the ophthalmic lens on or from the head of the human. In an embodiment, the spectacle structure includes a frame structure configured to position or support the ophthalmic lens on or from the head of the human.

In an embodiment, the vision correction device 210 is implanted in the eye 110 of the human. In an embodiment, the vision correction device is worn on the cornea 132 of the eye of the human. In an embodiment, the vision correction device includes a vision correction device configured to replace a natural lens in the eye of the human. In an embodiment, the vision correction device includes a vision correction device configured to at least partially correct a refractive error in the eye of the human. In an embodiment, the vision correction device is configured to optically compensate for a diminution of vision in the eye. In an embodiment, the vision correction device includes an electronically controllable vision parameter. In an embodiment, the transmitter circuit 830 is configured to broadcast the data indication of the presence and a characteristic of the ophthalmic lens 250.

In an embodiment, the data indicative of a characteristic of the ophthalmic lens 250 includes identification data of the ophthalmic lens, for example, such as brand name or manufacturer. In an embodiment, the data indicative of a characteristic of the ophthalmic lens includes focal length or index of refraction data of the ophthalmic lens. In an embodiment, the data indicative of a characteristic of the ophthalmic lens includes a parameter of the ophthalmic lens, such as spherical parameter data or cylindrical parameter data. In an embodiment, the data indicative of a characteristic of the ophthalmic lens includes optical transmissivity data of the ophthalmic lens.

In an embodiment, the transmitter circuit 830 is configured to broadcast data indicative of the presence of or a characteristic of the ophthalmic lens 250 in response to a query originated by an electronic device associated with the vision correction device 210. For example, the transmitter circuit may include an RFID.

In an embodiment, the ophthalmic lens 250 includes first ophthalmic lens configured to aid vision in a first eye of a human and a second ophthalmic lens configured to aid vision in a second eye of a human. In an embodiment, the wearable structure 852 includes a wearable structure configured to position or support the first ophthalmic lens in a first optical path incident on a first vision correction device placed in a first eye of the human and configured to position or support the second ophthalmic lens in a second optical path incident on a second vision correction device placed in a second eye of the human. In an embodiment, the transmitter circuit 830 is configured to broadcast data indicative of a first characteristic of the first ophthalmic lens and indicative of a second characteristic of the second ophthalmic lens.

All references cited herein are hereby incorporated by reference in their entirety or to the extent their subject matter is not otherwise inconsistent herewith.

In some embodiments, "configured" includes at least one of designed, set up, shaped, implemented, constructed, or adapted for at least one of a particular purpose, application, or function.

It will be understood that, in general, terms used herein, and especially in the appended claims, are generally intended as "open" terms. For example, the term "including" should be interpreted as "including but not limited to." For example, the term "having" should be interpreted as "having at least." For example, the term "has" should be interpreted as "having at least." For example, the term "includes" should be interpreted as "includes but is not limited to," etc. It will be further understood that if a specific number of an introduced claim recitation is intended, such an intent will be explicitly recited in the claim, and in the absence of such recitation no such intent is present. For example, as an aid to understanding, the following appended claims may contain usage of introductory phrases such as "at least one" or "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a receiver" should typically be interpreted to mean "at least one receiver"); the same holds true for the use of definite articles used to introduce claim recitations. In addition, even if a specific number of an introduced claim recitation is explicitly recited, it will be recognized that such recitation should typically be interpreted to mean at least the recited number (e.g., the bare recitation of "at least two chambers," or "a plurality of chambers," without other modifiers, typically means at least two chambers).

In those instances where a phrase such as "at least one of A, B, and C," "at least one of A, B, or C," or "an [item] selected from the group consisting of A, B, and C," is used, in general such a construction is intended to be disjunctive (e.g., any of these phrases would include but not be limited to systems that have A alone, B alone, C alone, A and B together, A and C together, B and C together, or A, B, and C together, and may further include more than one of A, B, or C, such as $A_1$, $A_2$, and C together, A, $B_1$, $B_2$, $C_1$, and $C_2$ together, or $B_1$ and $B_2$ together). It will be further understood that virtually any disjunctive word or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The herein described aspects depict different components contained within, or connected with, different other components. It is to be understood that such depicted architectures are merely examples and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable or physically interacting components or wirelessly interactable or wirelessly interacting components.

With respect to the appended claims the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Use of "Start," "End," "Stop," or the like blocks in the block diagrams is not intended to indicate a limitation on the beginning or end of any operations or functions in the diagram. Such flowcharts or diagrams may be incorporated into other flowcharts or diagrams where additional functions are performed before or after the functions shown in the diagrams of this application. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A vision correction system comprising:
a receiver circuit configured to receive data indicative of a presence of a wearable ophthalmic element in an optical path incident on a vision correction device, the vision correction device including an electronically controllable vision parameter and configured to be implanted in an eye of a human subject, wherein the vision correction device is configured to operate without the ophthalmic element and to adapt to the presence of the ophthalmic element being in the optical path; and
a controller circuit coupled to the vision correction device and configured to change the electronically controllable vision parameter of the vision correction device at least partially in response to the received data indicative of the presence of the wearable ophthalmic element in the optical path, operation of the vision correction device being adjusted to account for the presence of the wearable ophthalmic element in the optical path as determined by the receiver circuit responsive to the electronically controllable vision parameter being changed by the controller circuit.

2. The system of claim 1, wherein the receiver circuit is carried by the vision correction device.

3. The system of claim 1, wherein the data includes human-inputted data indicative of the presence of the wearable ophthalmic element in the optical path.

4. The system of claim 1, wherein the data includes a data signal indicative of the presence of the wearable ophthalmic element in the optical path.

5. The system of claim 4, wherein the data signal is originated by an electronic device associated with the wearable ophthalmic element.

6. The system of claim 4, wherein the data signal includes a radiofrequency band data signal, an ultrasound frequency band data signal, or an optical frequency band data signal.

7. The system of claim 4, wherein the data signal is transmitted by a sensor circuit configured to detect the presence of a wearable ophthalmic element in the optical path incident on the vision correction device.

8. The system of claim 1, wherein the data includes data indicative of a focal length, optical transmissivity, or an identification of the wearable ophthalmic element of the wearable ophthalmic element.

9. The system of claim 1, wherein the controller circuit is configured to correct a refractive error in the eye by changing the electronically controllable vision parameter of the vision correction device at least partially in response to the received data indicative of the presence of the wearable ophthalmic element in the optical path.

10. The system of claim 1, wherein the controller circuit is configured to not change the vision parameter of the vision correction device responsive to an override signal.

11. The system of claim 1, further comprising:
a transmitter circuit configured to broadcast data indicative of the presence of the wearable ophthalmic element in the optical path.

12. The system of claim 1, further comprising:
a wearable structure configured to position or support the wearable ophthalmic element in the optical path incident on the vision correction device; and
a transmitter circuit carried by the wearable structure and configured to broadcast data indicative of the presence of the wearable ophthalmic element in the optical path.

13. The system of claim 1, further comprising:
a wearable structure configured to position or support the wearable ophthalmic element in the optical path incident on the vision correction device; and
a human-interface circuit coupled to the wearable structure and configured to (i) receive a human-input indicative of a presence of the wearable ophthalmic element in the optical path, and (ii) broadcast data indicative of the presence of the wearable ophthalmic element in the optical path.

14. The system of claim 1, further comprising:
a sensor circuit configured to detect and transmit data indicative of the presence of the wearable ophthalmic element in the optical path.

15. The system of claim 1, further comprising:
a correction manager circuit configured to search an electronic database for a specified focal length of the wearable ophthalmic element.

16. The system of claim 15, wherein the controller circuit includes a controller circuit coupled to the vision correction device and configured to change a vision parameter of the vision correction device at least partially in response to the specified focal length of the wearable ophthalmic element.

17. The system of claim 1, further comprising:
a database stored on a non-transitory computer readable storage media and specifying a respective focal length of the wearable ophthalmic element for at least two identified wearable ophthalmic elements.

18. The system of claim 1, wherein the wearable ophthalmic element includes an eyeglass lens.

19. The system of claim 1, wherein the wearable ophthalmic element includes a contact lens.

20. A method of vision correction, the method comprising:
receiving data, by a receiving circuit, indicative of a presence of a wearable ophthalmic element in an optical path incident on a vision correction device implanted in an eye of a human subject, wherein the vision correction device is configured to operate without the ophthalmic element and to adapt to the presence of the ophthalmic element being in the optical path; and
changing, by a controller circuit, an electronically controllable vision parameter of the vision correction device at least partially in response to the received data indicative of the presence of the wearable ophthalmic element in the optical path.

21. The method of claim 20, further comprising:
broadcasting the data indicative of the presence of the wearable ophthalmic element in the optical path incident.

22. The method of claim 20, further comprising:
receiving a human-input indicative of the presence of the wearable ophthalmic element in the optical path; and
broadcasting data indicative of the presence of the wearable ophthalmic element in the optical path.

23. The method of claim 20, further comprising:
searching an electronic database for a specified focal length of the vision correction device correcting a refractive error in the eye if a particular identified wearable ophthalmic element is present in the optical path; and
changing a vision parameter of the vision correction device at least partially in response to the specified focal length of the vision correction device.

24. A vision correction system comprising:
an ophthalmic lens configured to aid vision in an eye of a human;

a wearable structure configured to position or support the ophthalmic lens in an optical path incident on a vision correction device implanted in the eye of the human, wherein the vision correction device is configured to operate without the ophthalmic lens being in the optical path and to adapt to a presence of the ophthalmic lens being in the optical path; and a transmitter circuit coupled to the wearable structure and configured to broadcast data indicative of the presence of the ophthalmic lens.

25. The system of claim 24, further comprising: a sensor circuit configured to detect if the wearable structure is being worn by the human.

26. The system of claim 25, wherein the sensor circuit is further configured to initiate the broadcast of data indicative of the presence of the ophthalmic lens by the transmitter circuit.

27. The system of claim 24, wherein the ophthalmic lens includes a single vision lens.

28. The system of claim 24, wherein the ophthalmic lens includes a bifocal vision lens.

29. The system of claim 24, wherein the wearable structure includes a spectacle structure configured to position or support the ophthalmic lens on or from the head of the human.

30. The system of claim 29, wherein the spectacle structure includes a frame structure configured to position or support the ophthalmic lens on or from the head of the human.

31. The system of claim 24, wherein the vision correction device is disposed on the eye of the human.

32. The system of claim 24, wherein the vision correction device is disposed on the cornea of the eye of the human.

33. The system of claim 24, wherein the vision correction device includes a vision correction device configured to at least partially correct a refractive error in the eye of the human.

34. The system of claim 24, wherein the vision correction device is configured to optically compensate for a diminution of vision in the eye.

35. The system of claim 24, wherein the vision correction device includes an electronically controllable vision parameter.

36. The system of claim 24, wherein the transmitter circuit is configured to broadcast data indication of a presence and a characteristic of the ophthalmic lens.

37. The system of claim 36, wherein the data indicative of a characteristic of the ophthalmic lens includes focal length data of the ophthalmic lens.

38. The system of claim 36, wherein the data indicative of a characteristic of the ophthalmic lens includes a parameter of the ophthalmic lens.

39. The system of claim 36, wherein the transmitter circuit is configured to broadcast data indicative of a presence or a characteristic of the ophthalmic lens in response to a query originated by an electronic device associated with the vision correction device.

40. The system of claim 24, wherein the ophthalmic lens includes first ophthalmic lens configured to aid vision in a first eye of a human and a second ophthalmic lens configured to aid vision in a second eye of a human.

41. The system of claim 40, wherein the wearable structure includes a wearable structure configured to position or support the first ophthalmic lens in a first optical path incident on a first vision correction device placed in a first eye of the human and configured to position or support the second ophthalmic lens in a second optical path incident on a second vision correction device placed in a second eye of the human.

42. The system of claim 40, wherein the transmitter circuit is configured to broadcast data indicative of a first characteristic of the first ophthalmic lens and indicative of a second characteristic of the second ophthalmic lens.

* * * * *